United States Patent [19]

Ballan

[11] Patent Number: 4,988,343
[45] Date of Patent: Jan. 29, 1991

[54] DRAINABLE POUCH FOR COLLECTING EXCRETIONS FROM THE HUMAN BODY
[75] Inventor: Akeel Ballan, Copenhagen, Denmark
[73] Assignee: Coloplast A/S, Denmark
[21] Appl. No.: 51,249
[22] Filed: May 15, 1987

Related U.S. Application Data

[63] Continuation-in-part of Ser. No. 820,093 Jan. 21, 1986, abandoned.

[30] Foreign Application Priority Data

Jan. 30, 1985 [DK] Denmark .............................. 406/85

[51] Int. Cl.$^5$ .............................................. A61F 5/44
[52] U.S. Cl. ....................................... 604/332; 383/66
[58] Field of Search ............................ 383/91, 66, 905; 604/332, 345

[56] References Cited

U.S. PATENT DOCUMENTS

| | | | |
|---|---|---|---|
| 1,857,010 | 5/1932 | Avery | 383/905 |
| 3,162,354 | 12/1964 | Frankel | 383/905 |
| 3,507,282 | 4/1970 | Burding | 604/333 |
| 3,690,320 | 9/1972 | Riely | 604/335 |
| 4,117,934 | 10/1978 | Mowli et al. | 383/905 |
| 4,394,955 | 7/1983 | Raines et al. | 383/905 |
| 4,561,858 | 12/1985 | Allen, Jr. et al. | 604/336 |

Primary Examiner—Randall L. Green
Assistant Examiner—Randy Shay
Attorney, Agent, or Firm—Howard L. Rose

[57] ABSTRACT

A drainable ostomy or similar pouch (22) is provided with a closing means (10) which in principle is a clip of known type encapsulated between two layers of plastic sheet material, preferably of the same kind as that constituting the pouch walls (24,26) which are joined together by a seam 28. At least one of the layers of plastic sheet material encapsulating the clip is integral with a pouch wall. If only one of the layers of sheet material encapsulating the clip is integral with the pouch wall, a discharge opening (34) of the pouch is situated at the very bottom of the pouch, between its walls. If both of the layers of sheet material is integral with the pouch walls, the discharge opening (34) is a slit adjacent a hot-melt seam serving to join the layers encapsulating the clip, between that seam and the remainder of the pouch wall in question.

5 Claims, 1 Drawing Sheet

DRAINABLE POUCH FOR COLLECTING EXCRETIONS FROM THE HUMAN BODY

This is a continuation of application Ser. No. 820,093, filed Jan. 21, 1986 now abandoned.

CROSS REFERENCE-TO RELATED APPLICATIONS

Applicant claims priority to Danish patent application No. 406185, filed Jan. 30, 1985.

Technical Field

The present invention relates to a drainable pouch for collecting excretions from natural and artificial discharge openings in the human body. Especially, the invention relates to drainable pouches for collecting excretions from enterostomies (e.g. colostomies and ileostomies), urine ostomies and incontinent natural urine discharge openings. The pouch comprises at least two walls of a smooth and flexible plastic sheet material joined together by a seam along the perimeter.

BACKGROUND OF THE INVENTION

Ostomy openings cannot be controlled at will, and in many cases patients with such surgically made openings or incontinent urine discharge openings are provided with a bag or pouch to collect the discharge from the openings. Many such pouches are disposable, i.e. for use only once, and the invention is not concerned with disposable pouches. In many other cases, however, it is preferred to use a drainable pouch provided with a discharge opening through which the pouch is emptied at more or less regular intervals. Many such pouches have been described, i.e. in the patent literature. The invention may be used in connection with any such known type of reusable collecting pouches. They are always provided with an inlet opening for the bodily excretions and around the inlet opening or elsewhere there is some device adapted to affix the pouch to the body of the patient. Moreover, there is frequently a venting aperture provided with a deodorizing filter to as to prevent bulging of the pouch due to intestinal gases. As the invention is not concerned with any such detail, they will not be discussed further.

The discharge opening of drainable pouches of the kind in question may be a slit in one of the pouch walls or, more commonly, merely an interruption of the seam joining the pouch walls together. As the main portion of the pouch is normally fairly wide, e.g. some 10 to 20 cm, it is usual to place the discharge opening in a narrower bottom extension of the pouch, e.g. having a width of some 4 to 6 cm. Moreover, it is common practice to close the discharge opening between the emptyings of the pouch by a clip, part of the narrower bottom portion being folded one or a few bends back and around the clip, the ends of which are doubled back over the folds of the bottom portion of the pouch. By experience such closing of the pouches is quite reliable.

The clips in question are usually strips made of a flexible yet relatively rigid and substantially unelastic material and in principle are wellknown, e.g. as closure means for all kinds of bags, e.g. for groceries or kitchen waste. They are frequently made of some rather rigid cellulosic material such as carton, or of some plastic material, and they are often reinforced with one or more metal threads.

In some cases the buyers of such drainable pouches use loose, independent clips. As these are easily lost in the process of emptying and possibly rinsing the pouch, it has been customary to glue or otherwise permanently affix the clip to the pouch adjacent the discharge opening thereof.

However, this has the drawback that the clip and especially the narrow spaces and edge portions around it unavoidably become dirty during the emptying the pouch; and while the latter can be easily rinsed and cleaned because of the smoothness of the plastic sheet from which it is made, so is not the case with the clip and its immediate surroundings. The contamination of the clip and its close surroundings is unhygienic and unpleasant for the user, especially for patients with ileostomies and colostomies, for whom the problem is particularly pertinent. Moreover, it may render is difficult to keep the underwear clean.

From FIG. 3 of the German published patent application DE 33 25 299 Al (having priorities from U.S. applications Nos. 398,913 and 491,256 of July 10, 1982, and May 3, 1983, respectively) there is known an ostomy pouch of the general type here concerned, having a narrowed bottom portion with the discharge opening right at the bottom of the bottom portion. A short distance above the discharge opening the bottom portion is provided with two lateral extensions, each forming a small pocket. The ends of a closing clip fits into and are placed in these pockets whereas the entire intermediate portion of the clip is free and situated at one of the walls of the pouch. Thus, when emptying the pouch, part of the waste material to remove may easily come into the space between the clip and the pouch wall. This can be avoided by removing the clip from the two pockets but firstly that in itself is unpleasant and may involve a risk of losing the clip; and moreover, waste material may easily come into the pockets in question, and it will be very difficult to rinse said small pockets since they have a width of the order of, e.g., 6-12 mm.

SUMMARY OF THE INVENTION

It is the object of the invention to avoid the drawbacks of prior art discussed.

The invention relates to a drainable pouch for collecting excretions from natural and artificial discharge openings in the human body, which pouch comprises at least two walls of a smooth and flexible plastic sheet material joined to each other by a seam along their perimeter and provided with a discharge opening adapted to be closed by a—preferably flat—clip made of a flexible yet comparatively rigid and substantially inelastic material. According to the invention the improvement of such a bag consists in that the clip in its entirety is enclosed between two layers of a smooth plastic sheet material compatible with that of which the pouch walls are made, said two layers being hermetically joined to each other by seams along and in close proximity to all edges of the clip, at least one of said two layers being integral with one of the pouch walls, the discharge opening of the pouch being adjacent and substantially parallel to the seam along one side edge of the clip, the ends of the clip and the plastic layers enclosing it extending beyond the discharge opening of the pouch.

As the clip is entirely surrounded by the layers of plastic sheet material and this material is smooth like the pouch walls, the portion of the pouch comprising the cl&p may be rinsed and cleaned with the same ease as other parts of the pouch and there is no risk of smudging the clip and its immediate surrounding.

A pouch as described in practice may exist in several embodiments. The two best embodiments known to the present inventor will be described in the following.

Seen from a point of view of manufacturing the pouch, the most practical embodiment is that each of the two layers of plastic sheet material enclosing the clip is integral with one pouch wall, the discharge opening of the pouch being a slit in one pouch wall between the seam along one side of the clip and the remainder of that pouch wall.

However, seen from the point of view of emptying the pouch, another embodiment may be more convenient, viz. an embodiment wherein only one of the two layers of plastic sheet material enclosing the clip is integral with a pouch wall whereby the discharge opening of the pouch simply is the bottom part thereof, the seam joining the two pouch walls being interrupted here.

DETAILED DESCRIPTION OF THE INVENTION

Figure 1:
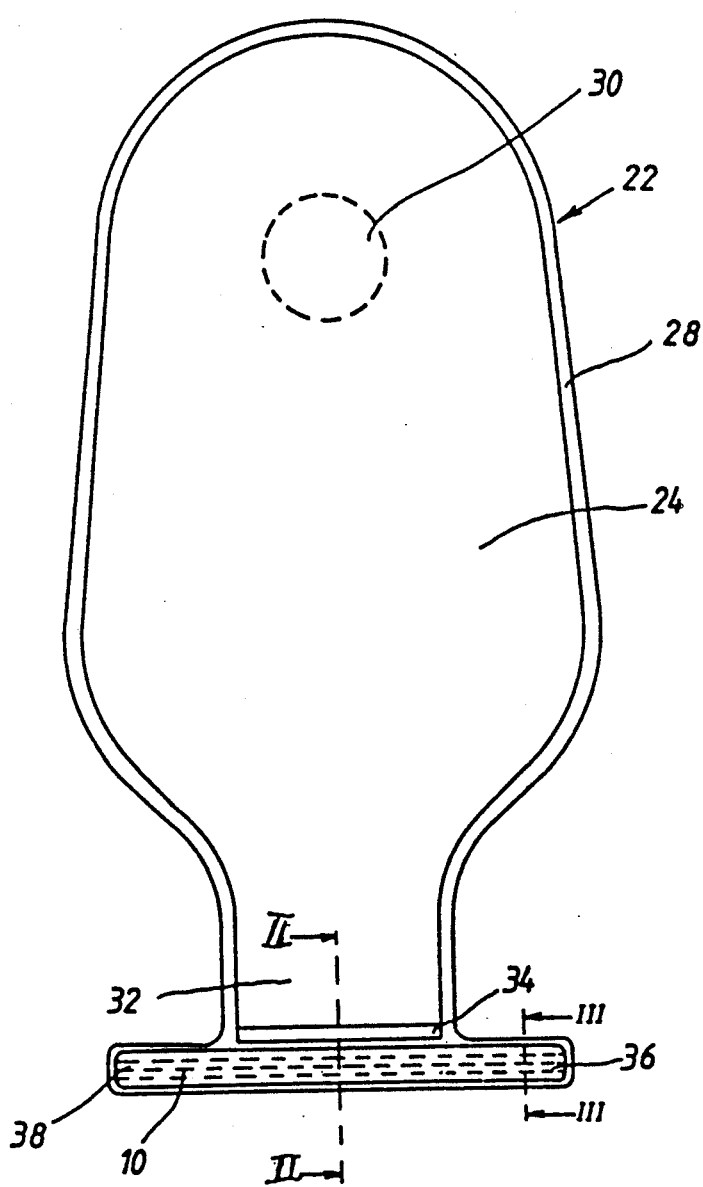
FIG. 1 is a plan view of an ostomy pouch according to the invention, seen from the side thereof which in use is turned away from the body of the user, FIG. 2 an enlarged sectional view along line II—II in FIG. 1, FIG. 3 an enlarged sectional view along line III—III in FIG. 1, and FIG. 4 an enlarged sectional view similar to that shown in FIG. 2, but of another embodiment of the invention.

The pouch or bag 22 shown in FIG. 1 is of a generally known and common type and comprises two walls 24,26 of a soft, smooth, flexible plastic sheet or foil material of any convenient polymer, as is wellknown in the art. The two walls have substantially the same outer contour and along that are joined together by means of a seam 28 made by hot-melting, glueing or in any other convenient manner. One of the walls (here wall 26) has an inlet opening for excretions and may be provided with any known and convenient means for affixing the pouch to the body of the user. The other wall 24 may in known manner be provided with a venting opening (not shown) provided with a deodorizing filter.

The shape of the pouch may be any convenient shape such as rectangular, elliptic or almost egg-shaped as shown in FIG. 1. Its lower portion 32 is normally much narrower than the remainder of the pouch, forming a sort of spout or nozzle through which the pouch is emptied at intervals. At the lowermost end of that narrower portion 32 or close thereto a discharge opening 34 is positioned. A closing device 10 is situated in close proximity to the discharge opening 34 and parallel thereto.

Figure 3:
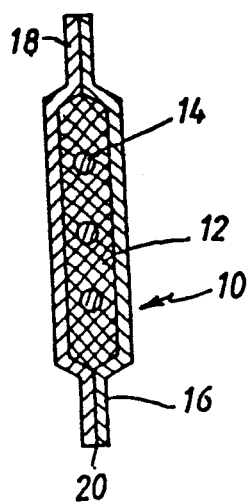

As is best seen in FIG. 3, the closing device 10 consists of a clip 12 of well-known type, consisting of a comparatively rigid, substantially inelastic strip which is reversibly bendable by the exertion of weak forces and may consist of a material such as carton, board or rather thick plastic strip material; in the embodiment shown the clip 12 is reinforced (in known manner) with three flexible but substantially inelastic metal threads 14.

Figure 2:
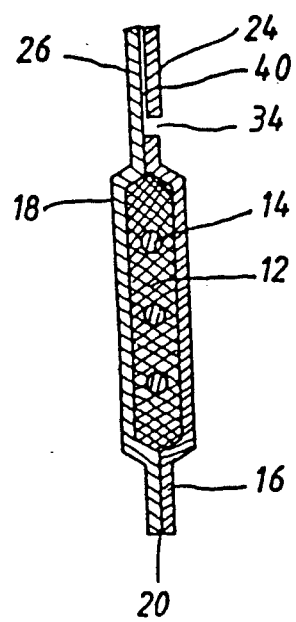
In FIGS. 2-4 the thickness dimension is substantially exaggerated compared to the length and width dimensions.
Figure 4:
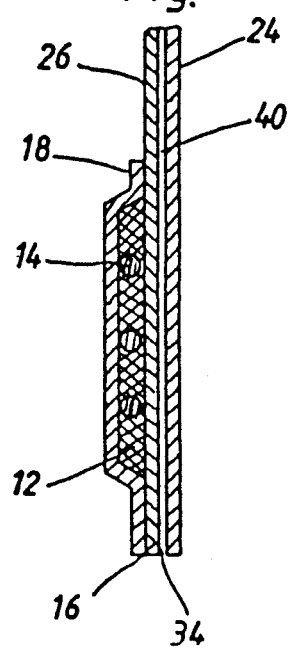

The clip 12 in its entirety is enclosed between two layers 16,18 of plastic foil or sheet material and the two layers 16 and 18 are hot-melted, welded, glued or some other way hermetically joined to each other by means of a seam 20 which in principle is of the same kind as the seam 28. The seam 20 does not necessarily extend inwardly to the very side and end edges of clip 12 as shown in FIGS. 2-4. There may well be a small space, e.g. 1 mm wide, between the edges of the clip and the seam 20.

As is seen in FIG. 1 the clip 12 with its envelope of layers 16,18 is longer than the width of the narrow portion 32 of the pouch 22 so that the ends 36,38 of the clip extend laterally beyond portion 32 and discharge opening 34. When the discharge opening is to be closed by means of closing device 10, the clip with its envelope is folded or "rolled" one or a few times parallel with its axis whereby discharge opening 34 is closed. Thereafter, the ends 36,38 of the clip 12 including its envelope 16,18 are bent over the farthest wall of the lower portion 32 of the pouch, which ensures that the discharge opening 34 remains closed until the opposite operations are carried out so as to make the pouch ready for being emptied. It should be noted that the length of the free ends 36,38 of the clip is not very critical. A length of each end 36,38 of $\frac{1}{3}-\frac{1}{2}$ of the width of lower portion 32 of the pouch will normally be convenient.

In the embodiment shown in FIGS. 1-2 the discharge opening 34 is a narrow slit, having a width of, e.g., 0-2 mm, in pouch wall 24, between seam 20 and the remainder of that pouch wall. The slit 34 is in open connection with the pouch space 40 between the pouch walls 24,26 as seen in FIG. 2 and the pouch may be emptied in the position shown in FIGS. 1-2.

In FIG. 2 it is seen that layer 18 of the envelope encasing clip 12 between the ends 36,38 is a mere prolongation of pouch wall 26, i.e. integral therewith. Layer 16 of the envelope encasing the clip is in principle integral with pouch wall 24 although the slit 34 in part interrupts the sheet adjacent slit 34 between ends 36,38. The slit 34 might be in pouch wall 26 instead of pouch wall 24.

The embodiment illustrated in FIG. 4 differs from that of FIGS. 1-2 in that layer 16 of the envelope 16,18 encasing clip 12 is a prolongation of pouch wall 26, i.e. is integral therewith, whereas layer 18 is separate from both pouch walls 24,26. Hereby the discharge opening 34 of the pouch is in its lowermost end, between the parts of pouch walls 24,26 that form the narrower portion 32 of the pouch. Instead of being integral with pouch wall 26, layer 16 might be integral with pouch wall 24.

It will be understood that it is within the scope of the invention to form layer 18 of the envelope 16,18 as shown in FIG. 4 merely by forming pouch wall 26 with a prolongation corresponding to the width of layer 18 and then, after having placed clip 12 in its correct position, doubling the prolongation back over the clip and hot melting the prolongation to the pouch wall adjacent the clip. An analogous manner of positioning layer 16 on clip 12 in FIG. 2 might be possible yet hardly very practical.

Some drainable ostomy pouches are provided a top opening for use when rinsing the pouch, especially in cases of ileostomy pouches. It goes without saying that such a top opening might be provided with a similar closing means 10 as that described hereinabove.

Layers 16,18 enclosing clip 12 must be of a sheet material compatible with that constituting pouch walls 24,26. In practice one will normally use same kind of sheet material for layers 16,18 and walls 24,26.

What is claimed is:

1. A device for collecting excretions from the human body, comprising:
    a drainable pouch, containing at least two walls of a smooth flexible sheet material sealed to each other along a seam disposed along the perimeter of said sealed walls, defining an inner and outer surface of said pouch,
    an inlet aperture in one of said walls,
    a discharge aperture between said pouch walls, being formed by an interruption of the seam joining the two pouch walls,
    a substantially inelastic, shape-retaining clip containing internally disposed reinforcing members, said clip being positioned parallel to said discharge aperture and in close proximity thereto, and having ends extending outwardly beyond said discharge aperture,
    flexible sheet material connected to said outer surface of said pouch, and hermetically sealed in a manner to surround and enclose said clip completely between said material and said outer surface of said pouch wall.

2. A device for collecting excretions, as in claim 1, wherein,
    said flexible sheet material is an extension of one of said pouch walls.

3. A reusable drainable pouch for collecting excretions from natural and artificial discharge openings in the human body, including:
    a pouch comprising at least two walls of a smooth and flexible sheet material joined to each other by a seam along their perimeter, said pouch having one portion narrower than the remainder of said pouch,
    an inlet opening in one of said walls for excretions,
    a discharge opening in said narrower portion of said pouch being adjacent and substantially parallel to the seam along one edge,
    a closing device incorporating a bendable substantially inelastic clip situated in close proximity to the discharge opening and parallel thereto, said clip being of a length greater than that of said discharge opening, and having ends extending beyond the discharge opening of said pouch, wherein the improvement comprises:
    said clip being hermetically enclosed around its entire outer perimeter between two layers of flexible sheet material, compatible with that of which the pouch walls are made, to provide a smooth continuous surface in the area of said discharge opening and said closing device for draining excretions from said pouch.

4. A reusable drainable pouch for collecting excretions from natural and artificial discharge openings as in claim 3, wherein,
    at least one of said two layers is integral with one pouch wall.

5. A reusable drainable pouch for collecting excretions from natural and artificial discharge openings, as in claim 3, wherein,
    one of said layers is integral with one of said pouch walls, and the other layer is integral with another of said pouch walls.

* * * * *